US007888077B2

(12) United States Patent
Filippov et al.

(10) Patent No.: US 7,888,077 B2
(45) Date of Patent: Feb. 15, 2011

(54) **METHOD FOR PRODUCING AN L-AMINO ACID USING A BACTERIUM OF THE *ENTEROBACTERIACEAE* FAMILY WITH ATTENUATED EXPRESSION OF THE *KEFB* GENE**

(75) Inventors: Dmitriy Vladimirovich Filippov, Moscow (RU); Elvira Borisovna Voroshilova, Moscow (RU); Mikhail Markovich Gusyatiner, Moscow (RU)

(73) Assignee: Ajinomoto., Inc., Tokyo (JP)

( * ) Notice: Subject to any disclaimer, the term of this patent is extended or adjusted under 35 U.S.C. 154(b) by 419 days.

(21) Appl. No.: 11/934,890

(22) Filed: Nov. 5, 2007

(65) Prior Publication Data

US 2009/0226980 A1    Sep. 10, 2009

Related U.S. Application Data

(63) Continuation of application No. PCT/JP2006/309987, filed on May 12, 2006.

(60) Provisional application No. 60/736,830, filed on Nov. 16, 2005.

(30) Foreign Application Priority Data

May 16, 2005   (RU) .............................. 2005114823

(51) Int. Cl.
*C12P 13/24* (2006.01)
*C12P 13/22* (2006.01)
*C12P 13/20* (2006.01)
*C12P 13/14* (2006.01)
*C12P 13/12* (2006.01)
*C12P 13/10* (2006.01)
*C12P 13/08* (2006.01)
*C12N 1/20* (2006.01)
*C07H 21/04* (2006.01)

(52) U.S. Cl. ..................... 435/107; 435/108; 435/109; 435/110; 435/113; 435/114; 435/115; 435/116; 435/252.33; 536/23.2

(58) Field of Classification Search ...................... None
See application file for complete search history.

(56) References Cited

U.S. PATENT DOCUMENTS

| 7,138,266 | B2 | 11/2006 | Debabov et al. |
| 7,259,003 | B2 | 8/2007 | Livshits et al. |
| 2005/0112731 | A1 | 5/2005 | Kashiwagi et al. |
| 2005/0214911 | A1 | 9/2005 | Marchenko et al. |
| 2005/0239175 | A1 | 10/2005 | Tabolina et al. |
| 2006/0088919 | A1 | 4/2006 | Rybak et al. |
| 2006/0160192 | A1 | 7/2006 | Rybak et al. |
| 2006/0286643 | A1 | 12/2006 | Sheremet'eva et al. |

FOREIGN PATENT DOCUMENTS

| WO | WO2004/080386 | 9/2004 |
| WO | WO2004/090125 | 10/2004 |

OTHER PUBLICATIONS

Cha et al. Appl Environ Microbiol. Jan. 1997;63(1):71-6. Identification and characterization of a *Pantoea citrea* gene encoding glucose dehydrogenase that is essential for causing pink disease of pineapple.*
Whisstock et al. Quaterly Reviews of Biophysics, 2003, "Prediction of protein function from protein sequence and structure", 36(3): 307-340.*
Chica et al. Semi-rational approaches to engineering enzyme activity: combining the benefits of directed evolution and rational design, Curr Opin Biotechnol. Aug. 2005;16(4):378-84. Review.*
Witkowski et al. Conversion of a beta-ketoacyl synthase to a malonyl decarboxylase by replacement of the active-site cysteine with glutamine, Biochemistry. Sep 7, 1999;38(36):11643-50.*
International Preliminary Report on Patentability for PCT Patent App. No. PCT/JP2006/309987 (Nov. 29, 2007).
Bakker, E., et al., "Evidence for Multiple $K^+$Export Systems in *Escherichia coli*," J. Bacteriol. 1987;169(8):3743-3749.
Ferguson, G. P., et al., "Activation of potassium channels during metabolite detoxification in *Escherichia coli*," Mol. Microbiol. 1993;9(6):1297-1303.
Ferguson, G. P., et al., "Potassium channel activation by glutathione-S-conjugates in *Escherichia coli*: protection against methylglyoxal is mediated by cytoplasmic acidification," Mol. Microbiol. 1995;17(6):1025-1033.
Ferguson, G. P., et al., "Survival during Exposure to the Electrophile Reagent N-Ethylmaleimide in *Escherichia coli*: Role of KefB and KefC Potassium Channels," J. Bacteriol. 1997;179(4):1007-1012.
Ness, L. S., et al., "Different Foci for the Regulation of the Activity of the KefB and KefC Glutathione-gated $K^+$Efflux Systems," J. Biol. Chem. 1999;274(14):9524-9530.
Epstein, W., "The Roles and Regulation of Potassium in Bacteria," Prog. Nuc. Acid Res. and Mol. Biol. 2003;75:293-320.
International Search Report for PCT Patent App. No. PCT/JP2006/309987 (Oct. 6, 2006).

* cited by examiner

*Primary Examiner*—Robert B Mondesi
*Assistant Examiner*—Iqbal H Chowdhury
(74) *Attorney, Agent, or Firm*—Shelly Guest Cermak; Cermak Nakajima LLP

(57) ABSTRACT

The present invention provides a method for producing an L-amino acid using a bacterium of the Enterobacteriaceae family, particularly a bacterium belonging to the genus *Escherichia* or *Pantoea*, which has been modified to attenuate expression of the kefB gene.

6 Claims, 2 Drawing Sheets

SEQUENCE LISTING

```
<160> NUMBER OF SEQ ID NOS: 6

<210> SEQ ID NO 1
<211> LENGTH: 1806
<212> TYPE: DNA
<213> ORGANISM: Escherichia coli
<220> FEATURE:
<221> NAME/KEY: CDS
<222> LOCATION: (1)..(1806)

<400> SEQUENCE: 1 atg gaa ggt tcc gat ttt tta ctc gca gga gtg ctg ttt ctc ttc gcg      48
Met Glu Gly Ser Asp Phe Leu Leu Ala Gly Val Leu Phe Leu Phe Ala
1               5                   10                  15 gcg gtg gct gcg gtg ccg ctg gca tcg cgg ctg ggt att ggc gct gtg      96
Ala Val Ala Ala Val Pro Leu Ala Ser Arg Leu Gly Ile Gly Ala Val
                20                  25                  30 ttg gga tat ttg ctg gca ggg att gca att ggc ccg tgg ggg ctg ggg     144
Leu Gly Tyr Leu Leu Ala Gly Ile Ala Ile Gly Pro Trp Gly Leu Gly
        35                  40                  45 ttt att agc gac gtc gat gag atc ctc cac ttt tcg gaa ctc ggc gtg     192
Phe Ile Ser Asp Val Asp Glu Ile Leu His Phe Ser Glu Leu Gly Val
    50                  55                  60
```

| | | |
|---|---|---|
| gta ttc ctg atg ttt atc atc ggc ctt gag ttg aat ccc tcc aaa ctt<br>Val Phe Leu Met Phe Ile Ile Gly Leu Glu Leu Asn Pro Ser Lys Leu<br>65                            70                      75                      80 | 240 |
| tgg caa ctg cgg cgt tcg att ttt ggc gta ggc gcg gca cag gtg ctg<br>Trp Gln Leu Arg Arg Ser Ile Phe Gly Val Gly Ala Ala Gln Val Leu<br>                      85                      90                      95 | 288 |
| tta agc gcg gcg ttg ctg gcg gga tta ttg atg ctg acg gat ttc gcc<br>Leu Ser Ala Ala Leu Leu Ala Gly Leu Leu Met Leu Thr Asp Phe Ala<br>           100                      105                      110 | 336 |
| tgg cag gcg gcg gtg gtc ggt ggc att ggc ctt gcg atg tct tca act<br>Trp Gln Ala Ala Val Val Gly Gly Ile Gly Leu Ala Met Ser Ser Thr<br>115                          120                      125 | 384 |
| gca atg gcg ttg caa ttg atg cgt gag aaa ggg atg aat cgc agc gaa<br>Ala Met Ala Leu Gln Leu Met Arg Glu Lys Gly Met Asn Arg Ser Glu<br>        130                      135                      140 | 432 |
| tcc ggc cag ctc ggg ttt tcg gtt ctg ctg ttt cag gat ctg gca gta<br>Ser Gly Gln Leu Gly Phe Ser Val Leu Leu Phe Gln Asp Leu Ala Val<br>145                          150                      155                      160 | 480 |
| atc cca gca ctg gcg tta gtg ccg ttg ttg gcg ggg tcg gca gac gaa<br>Ile Pro Ala Leu Ala Leu Val Pro Leu Leu Ala Gly Ser Ala Asp Glu<br>                165                      170                      175 | 528 |
| cat ttc gac tgg atg aag gtc ggc atg aag gtg ctg gcg ttt gtc ggc<br>His Phe Asp Trp Met Lys Val Gly Met Lys Val Leu Ala Phe Val Gly<br>                      180                      185                      190 | 576 |
| atg ctg att ggt ggg cgc tat tta ctg cgt ccg gta ttc cgc ttt att<br>Met Leu Ile Gly Gly Arg Tyr Leu Leu Arg Pro Val Phe Arg Phe Ile<br>           195                      200                      205 | 624 |
| gca gct tct ggc gtg cgg gaa gtg ttc acc gcc gcg acg ctg ctg ctg<br>Ala Ala Ser Gly Val Arg Glu Val Phe Thr Ala Ala Thr Leu Leu Leu<br>        210                      215                      220 | 672 |
| gtg ttg ggt tcc gca ttg ttt atg gat gcg ctg ggg ctg tcg atg gcg<br>Val Leu Gly Ser Ala Leu Phe Met Asp Ala Leu Gly Leu Ser Met Ala<br>225                          230                      235                      240 | 720 |
| ctc ggt aca ttt att gcg ggc gtg ctg ctg gcg gaa agt gaa tat cgc<br>Leu Gly Thr Phe Ile Ala Gly Val Leu Leu Ala Glu Ser Glu Tyr Arg<br>                      245                      250                      255 | 768 |
| cat gaa ctg gaa acg gct atc gat ccc ttc aaa ggc ttg ctg ctc ggt<br>His Glu Leu Glu Thr Ala Ile Asp Pro Phe Lys Gly Leu Leu Leu Gly<br>        260                      265                      270 | 816 |
| ttg ttc ttt atc tct gtc ggc atg tca ctc aac ctc ggg gtg ctt tat<br>Leu Phe Phe Ile Ser Val Gly Met Ser Leu Asn Leu Gly Val Leu Tyr<br>275                          280                      285 | 864 |
| acc cat ctg ttg tgg gta gtg ata agc gtg gtt gtg ctg gtg gcg gtg<br>Thr His Leu Leu Trp Val Val Ile Ser Val Val Val Leu Val Ala Val<br>        290                      295                      300 | 912 |
| aaa att ctc gtg ctg tat ctg ctg gcg cga ttg tat ggc gtg cgt agc<br>Lys Ile Leu Val Leu Tyr Leu Leu Ala Arg Leu Tyr Gly Val Arg Ser<br>305                          310                      315                      320 | 960 |
| tca gag cgg atg cag ttt gct ggc gtg ttg agt cag ggt ggt gag ttt<br>Ser Glu Arg Met Gln Phe Ala Gly Val Leu Ser Gln Gly Gly Glu Phe<br>                      325                      330                      335 | 1008 |
| gcc ttt gtc ctc ttt tct acc gct tct tca caa cgc tta ttc cag ggc<br>Ala Phe Val Leu Phe Ser Thr Ala Ser Ser Gln Arg Leu Phe Gln Gly<br>        340                      345                      350 | 1056 |
| gac cag atg gcg ttg ttg ctg gtg acg gtg acg ctt tcc atg atg acc<br>Asp Gln Met Ala Leu Leu Leu Val Thr Val Thr Leu Ser Met Met Thr<br>355                          360                      365 | 1104 |
| acg ccg ttg ctg atg aag ctg gtg gat aaa tgg cta tcc cgc cag ttt<br>Thr Pro Leu Leu Met Lys Leu Val Asp Lys Trp Leu Ser Arg Gln Phe<br>        370                      375                      380 | 1152 |

```
aac gga ccg gaa gaa gaa gac gaa aaa ccg tgg gtc aac gat gat aaa    1200
Asn Gly Pro Glu Glu Glu Asp Glu Lys Pro Trp Val Asn Asp Asp Lys
385                 390                 395                 400 ccc cag gtc att gtc gtg ggc ttc ggg cgt ttt ggt cag gtg att ggt    1248
Pro Gln Val Ile Val Val Gly Phe Gly Arg Phe Gly Gln Val Ile Gly
                405                 410                 415 cgt ttg ctg atg gca aat aaa atg cgc att acc gtg ctg gag cgg gat    1296
Arg Leu Leu Met Ala Asn Lys Met Arg Ile Thr Val Leu Glu Arg Asp
            420                 425                 430 atc agc gcc gtt aac ctg atg cgt aaa tac ggc tac aaa gtt tat tac    1344
Ile Ser Ala Val Asn Leu Met Arg Lys Tyr Gly Tyr Lys Val Tyr Tyr
        435                 440                 445 ggc gac gcc acg cag gtc gat ctt tta cgt tct gcg ggt gca gag gcc    1392
Gly Asp Ala Thr Gln Val Asp Leu Leu Arg Ser Ala Gly Ala Glu Ala
    450                 455                 460 gct gag tct atc gtc att acc tgt aac gag ccg gaa gac acc atg aag    1440
Ala Glu Ser Ile Val Ile Thr Cys Asn Glu Pro Glu Asp Thr Met Lys
465                 470                 475                 480 ctg gtg gaa ata tgc caa cag cac ttt ccg cat ttg cat att ctt gcg    1488
Leu Val Glu Ile Cys Gln Gln His Phe Pro His Leu His Ile Leu Ala
                485                 490                 495 cga gcg cgc gga cgt gtg gaa gcg cat gag tta tta cag gca ggg gtg    1536
Arg Ala Arg Gly Arg Val Glu Ala His Glu Leu Leu Gln Ala Gly Val
            500                 505                 510 acg cag ttt tcc cgt gaa aca ttc tcc agt gcg tta gag ctg ggg cgc    1584
Thr Gln Phe Ser Arg Glu Thr Phe Ser Ser Ala Leu Glu Leu Gly Arg
        515                 520                 525 aag acg ctg gtc acg ctt ggc atg cat ccg cat cag gca cag cga gcg    1632
Lys Thr Leu Val Thr Leu Gly Met His Pro His Gln Ala Gln Arg Ala
    530                 535                 540 caa ctg cat ttt cgc cgc ctg gat atg cgg atg ctg cga gag ctc atc    1680
Gln Leu His Phe Arg Arg Leu Asp Met Arg Met Leu Arg Glu Leu Ile
545                 550                 555                 560 cca atg cat gcc gat acc gta caa att tct cgc gcc agg gaa gcc cga    1728
Pro Met His Ala Asp Thr Val Gln Ile Ser Arg Ala Arg Glu Ala Arg
                565                 570                 575 cgc gaa ctg gaa gag att ttc cag cgt gaa atg caa caa gaa cga cgc    1776
Arg Glu Leu Glu Glu Ile Phe Gln Arg Glu Met Gln Gln Glu Arg Arg
            580                 585                 590 cag ctg gac ggc tgg gat gaa ttt gag tag                            1806
Gln Leu Asp Gly Trp Asp Glu Phe Glu
        595                 600

<210> SEQ ID NO 2
<211> LENGTH: 601
<212> TYPE: PRT
<213> ORGANISM: Escherichia coli

<400> SEQUENCE: 2

Met Glu Gly Ser Asp Phe Leu Leu Ala Gly Val Leu Phe Leu Phe Ala
1               5                   10                  15

Ala Val Ala Ala Val Pro Leu Ala Ser Arg Leu Gly Ile Gly Ala Val
                20                  25                  30

Leu Gly Tyr Leu Leu Ala Gly Ile Ala Ile Gly Pro Trp Gly Leu Gly
            35                  40                  45

Phe Ile Ser Asp Val Asp Glu Ile Leu His Phe Ser Glu Leu Gly Val
        50                  55                  60

Val Phe Leu Met Phe Ile Ile Gly Leu Glu Leu Asn Pro Ser Lys Leu
65                  70                  75                  80
```

-continued

```
Trp Gln Leu Arg Arg Ser Ile Phe Gly Val Gly Ala Ala Gln Val Leu
                    85                  90                  95

Leu Ser Ala Ala Leu Leu Ala Gly Leu Leu Met Leu Thr Asp Phe Ala
            100                 105                 110

Trp Gln Ala Ala Val Val Gly Gly Ile Gly Leu Ala Met Ser Ser Thr
        115                 120                 125

Ala Met Ala Leu Gln Leu Met Arg Glu Lys Gly Met Asn Arg Ser Glu
    130                 135                 140

Ser Gly Gln Leu Gly Phe Ser Val Leu Leu Phe Gln Asp Leu Ala Val
145                 150                 155                 160

Ile Pro Ala Leu Ala Leu Val Pro Leu Leu Ala Gly Ser Ala Asp Glu
                165                 170                 175

His Phe Asp Trp Met Lys Val Gly Met Lys Val Leu Ala Phe Val Gly
            180                 185                 190

Met Leu Ile Gly Gly Arg Tyr Leu Leu Arg Pro Val Phe Arg Phe Ile
        195                 200                 205

Ala Ala Ser Gly Val Arg Glu Val Phe Thr Ala Ala Thr Leu Leu Leu
    210                 215                 220

Val Leu Gly Ser Ala Leu Phe Met Asp Ala Leu Gly Leu Ser Met Ala
225                 230                 235                 240

Leu Gly Thr Phe Ile Ala Gly Val Leu Leu Ala Glu Ser Glu Tyr Arg
                245                 250                 255

His Glu Leu Glu Thr Ala Ile Asp Pro Phe Lys Gly Leu Leu Leu Gly
            260                 265                 270

Leu Phe Phe Ile Ser Val Gly Met Ser Leu Asn Leu Gly Val Leu Tyr
        275                 280                 285

Thr His Leu Leu Trp Val Val Ile Ser Val Val Leu Val Ala Val
    290                 295                 300

Lys Ile Leu Val Leu Tyr Leu Leu Ala Arg Leu Tyr Gly Val Arg Ser
305                 310                 315                 320

Ser Glu Arg Met Gln Phe Ala Gly Val Leu Ser Gln Gly Gly Glu Phe
                325                 330                 335

Ala Phe Val Leu Phe Ser Thr Ala Ser Ser Gln Arg Leu Phe Gln Gly
            340                 345                 350

Asp Gln Met Ala Leu Leu Leu Val Thr Val Thr Leu Ser Met Met Thr
        355                 360                 365

Thr Pro Leu Leu Met Lys Leu Val Asp Lys Trp Leu Ser Arg Gln Phe
    370                 375                 380

Asn Gly Pro Glu Glu Glu Asp Glu Lys Pro Trp Val Asn Asp Asp Lys
385                 390                 395                 400

Pro Gln Val Ile Val Gly Phe Gly Arg Phe Gly Gln Val Ile Gly
                405                 410                 415

Arg Leu Leu Met Ala Asn Lys Met Arg Ile Thr Val Leu Glu Arg Asp
            420                 425                 430

Ile Ser Ala Val Asn Leu Met Arg Lys Tyr Gly Tyr Lys Val Tyr Tyr
        435                 440                 445

Gly Asp Ala Thr Gln Val Asp Leu Leu Arg Ser Ala Gly Ala Glu Ala
    450                 455                 460

Ala Glu Ser Ile Val Ile Thr Cys Asn Glu Pro Glu Asp Thr Met Lys
465                 470                 475                 480
```

Leu Val Glu Ile Cys Gln Gln His Phe Pro His Leu His Ile Leu Ala
            485                 490                 495

Arg Ala Arg Gly Arg Val Glu Ala His Glu Leu Leu Gln Ala Gly Val
            500                 505                 510

Thr Gln Phe Ser Arg Glu Thr Phe Ser Ser Ala Leu Glu Leu Gly Arg
            515                 520                 525

Lys Thr Leu Val Thr Leu Gly Met His Pro His Gln Ala Gln Arg Ala
            530                 535                 540

Gln Leu His Phe Arg Arg Leu Asp Met Arg Met Leu Arg Glu Leu Ile
545                 550                 555                 560

Pro Met His Ala Asp Thr Val Gln Ile Ser Arg Ala Arg Glu Ala Arg
            565                 570                 575

Arg Glu Leu Glu Glu Ile Phe Gln Arg Glu Met Gln Glu Arg Arg
            580                 585                 590

Gln Leu Asp Gly Trp Asp Glu Phe Glu
            595                 600

<210> SEQ ID NO 3
<211> LENGTH: 57
<212> TYPE: DNA
<213> ORGANISM: Artificial
<220> FEATURE:
<223> OTHER INFORMATION: primer

<400> SEQUENCE: 3
ctggctggca atccgctgt ctccaggagg ccgctgtagt aagccagtat acactcc         57

<210> SEQ ID NO 4
<211> LENGTH: 57
<212> TYPE: DNA
<213> ORGANISM: Artificial
<220> FEATURE:
<223> OTHER INFORMATION: primer

<400> SEQUENCE: 4
cgcaataaaa cgttttcgga ttgccatctt tacccttaa gggcaccaat aactgcc         57

<210> SEQ ID NO 5
<211> LENGTH: 21
<212> TYPE: DNA
<213> ORGANISM: Artificial
<220> FEATURE:
<223> OTHER INFORMATION: primer

<400> SEQUENCE: 5
aaagtgctta ccgttatgac g                                              21

<210> SEQ ID NO 6
<211> LENGTH: 20
<212> TYPE: DNA
<213> ORGANISM: Artificial
<220> FEATURE:
<223> OTHER INFORMATION: primer

<400> SEQUENCE: 6
tgaatcctgc gcctgacagg                                                20

US 7,888,077 B2

METHOD FOR PRODUCING AN L-AMINO ACID USING A BACTERIUM OF THE *ENTEROBACTERIACEAE* FAMILY WITH ATTENUATED EXPRESSION OF THE *KEFB* GENE

This application is a continuation under 35 U.S.C. §120 of PCT Patent Application No. PCT/JP2006/309987, filed May 12, 2006. This application also claims priority under 35 U.S.C. §119 to Russian Patent Application No. 2005114823, filed May 16, 2005, and U.S. Provisional Patent Application No. 60/736,830, filed Nov. 16, 2005. All of these documents are hereby incorporated by reference. The Sequence Listing filed electronically herewith is also hereby incorporated by reference in its entirety (File Name: US-226_Seq_List_Copy__1; File Size: 15 KB; Date Created: Nov. 5, 2007).

BACKGROUND OF THE INVENTION

1. Field of the Invention

The present invention relates to the microbiological industry, and specifically to a method for producing an L-amino acid using a bacterium of the Enterobacteriaceae family which has been modified to attenuate expression of the kefB gene.

2. Brief Description of the Related Art

The KefB protein encoded by the kefB gene is a potassium transporter which belongs to the CPA2 family of monovalent cation/proton antiporters. The KefB potassium efflux system is regulated by glutathione and plays a role in responding to changes in osmotic pressure and in protecting the cell from electrophile toxicity. Potassium efflux by KefB is activated by adducts formed by the reaction of glutathione with electrophilic compounds such as methylglyoxal and chlorodinitrobenzene (Ferguson, G. P. et al., Mol. Microbiol., 1993, 9(6):1297-1303). Potassium efflux mediated by KefB leads to acidification of the cytoplasm, which protects the cell from electrophile toxicity (Ferguson, G. P. et al., Mol. Microbiol., 1995, 17 (6):1025-1033; Ferguson, G. P. et al., J. Bacteriol. 1997, 179(4):1007-1012). KefB is highly similar to KefC, an additional potassium efflux system, at the level of both their primary sequences and domain organization. Despite the high degree of sequence similarity, KefB and KefC exhibit different sensitivities to the same site-specific mutations (Ness, L. S. and Booth, I. R., J. Biol. Chem., 1999, 274(14):9524-9530). In addition to KefB and KefC, an unidentified potassium efflux system exists, capable of mediating a high rate of $K^+$ efflux (Bakker, E. P. et al., J. Bacteriol., 1987, 169 (8): 3743-3749).

But currently, there have been no reports of inactivating the kefB gene for the purpose of producing L-amino acids.

SUMMARY OF THE INVENTION

Objects of the present invention include enhancing the productivity of L-amino acid-producing strains and providing a method for producing an L-amino acid using these strains.

The above objects were achieved by finding that attenuating expression of the kefB gene can enhance production of L-amino acids, such as L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, L-arginine, L-phenylalanine, L-tyrosine, and L-tryptophan.

The present invention provides a bacterium of the Enterobacteriaceae family having an increased ability to produce amino acids, such as L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, L-arginine, L-phenylalanine, L-tyrosine, and L-tryptophan.

It is an object of the present invention to provide an L-amino acid-producing bacterium of the Enterobacteriaceae family, wherein the bacterium has been modified to attenuate expression of the kefB gene.

It is a further object of the present invention to provide the bacterium as described above, wherein the expression of the kefB gene is attenuated by inactivation of the kefB gene.

It is a further object of the present invention to provide the bacterium as described above, wherein the bacterium belongs to the genus *Escherichia*.

It is a further object of the present invention to provide the bacterium as described above, wherein the bacterium belongs to the genus *Pantoea*.

It is a further object of the present invention to provide the bacterium as described above, wherein said L-amino acid is selected from the group consisting of an aromatic L-amino acid and a non-aromatic L-amino acid.

It is a further object of the present invention to provide the bacterium as described above, wherein said aromatic L-amino acid is selected from the group consisting of L-phenylalanine, L-tyrosine, and L-tryptophan.

It is a further object of the present invention to provide the bacterium as described above, wherein said non-aromatic L-amino acid is selected from the group consisting of L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, and L-arginine.

It is a further object of the present invention to provide a method for producing an L-amino acid comprising:

cultivating the bacterium as described above in a medium, and collecting said L-amino acid from the medium.

It is a further object of the present invention to provide the method as described above, wherein said L-amino acid is selected from the group consisting of an aromatic L-amino acid and a non-aromatic L-amino acid.

It is a further object of the present invention to provide the method as described above, wherein said aromatic L-amino acid is selected from the group consisting of L-phenylalanine, L-tyrosine, and L-tryptophan.

It is a further object of the present invention to provide the method as described above, wherein said non-aromatic L-amino acid is selected from the group consisting of L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, and L-arginine.

The present invention is described in detail below.

DESCRIPTION OF THE PREFERRED EMBODIMENTS

1. Bacterium of the Present Invention

Figure 1:
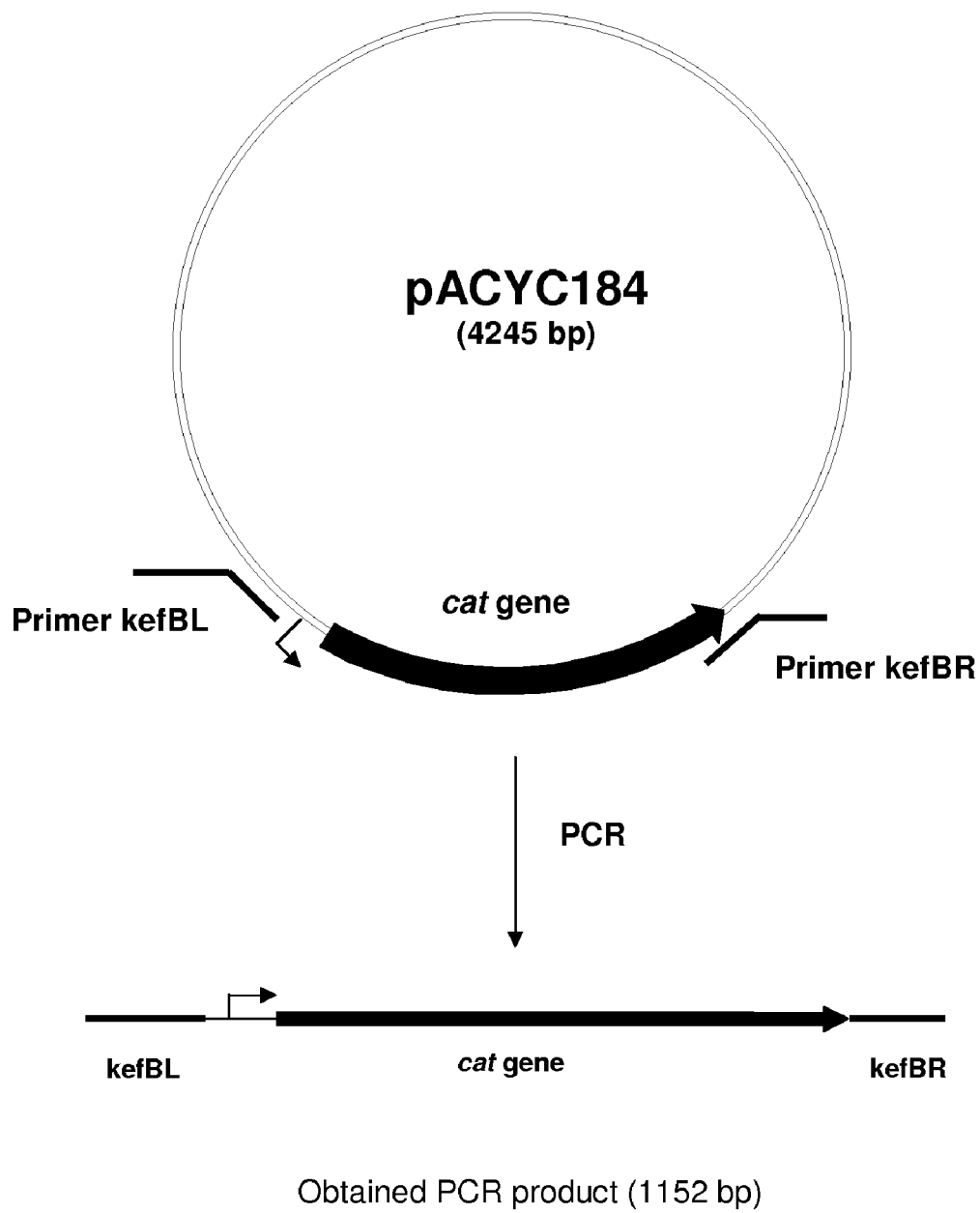
FIG. 1 shows the relative positions of primers kefBL and kefBR on plasmid pACYC184, which is used for amplification of the cat gene.

The bacterium of the present invention is an L-amino acid-producing bacterium of the Enterobacteriaceae family, wherein the bacterium has been modified to attenuate expression of the kefB gene.

In the present invention, "L-amino acid-producing bacterium" means a bacterium which has an ability to produce and excrete an L-amino acid into a medium, when the bacterium is cultured in the medium.

The term "L-amino acid-producing bacterium" as used herein also means a bacterium which is able to produce and cause accumulation of an L-amino acid in a culture medium in an amount larger than by a wild-type or parental strain of the bacterium, for example, *E. coli*, such as *E. coli* K-12, and preferably means that the bacterium is able to cause accumulation in a medium of an amount not less than 0.5 g/L, more preferably not less than 1.0 g/L, of the target L-amino acid. The term "L-amino acid" includes L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine, and L-valine.

The term "aromatic L-amino acid" includes L-phenylalanine, L-tyrosine, and L-tryptophan. The term "non-aromatic L-amino acid" includes L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, and L-arginine. L-threonine, L-lysine, L-cysteine, L-leucine, L-histidine, L-glutamic acid, L-phenylalanine, L-tryptophan, L-proline and L-arginine are particularly preferred.

The Enterobacteriaceae family includes bacteria belonging to the genera *Escherichia*, *Enterobacter*, *Erwinia*, *Klebsiella*, *Pantoea*, *Photorhabdus*, *Providencia*, *Salmonella*, *Serratia*, *Shigella*, *Morganella* *Yersinia*, etc. Specifically, those classified into the Enterobacteriaceae according to the taxonomy used by the NCBI (National Center for Biotechnology Information) database (www.ncbi.nlm.nih.gov/Taxonomy/Browser/wwwtax.cgi?id=91347) can be used. A bacterium belonging to the genus *Escherichia* or *Pantoea* is preferred.

The phrase "a bacterium belonging to the genus *Escherichia*" means that the bacterium is classified into the genus *Escherichia* according to the classification known to a person skilled in the art of microbiology. Examples of a bacterium belonging to the genus *Escherichia* as used in the present invention include, but are not limited to, *Escherichia coli* (*E. coli*).

The bacterium belonging to the genus *Escherichia* that can be used in the present invention is not particularly limited; however, e.g., bacteria described by Neidhardt, F. C. et al. (*Escherichia coli* and *Salmonella typhimurium*, American Society for Microbiology, Washington D.C., 1208, Table 1) are encompassed by the present invention.

The phrase "a bacterium belonging to the genus *Pantoea*" means that the bacterium is classified into the genus *Pantoea* according to the classification known to a person skilled in the art of microbiology. Some species of *Enterobacter agglomerans* have been recently re-classified into *Pantoea agglomerans*, *Pantoea ananatis*, *Pantoea stewartii* or the like, based on the nucleotide sequence analysis of 16S rRNA, etc. (Int. J. Syst. Bacteriol., 43, 162-173 (1993)).

The phrase "bacterium has been modified to attenuate expression of the kefB gene" means that the bacterium has been modified in such a way that the modified bacterium contains a reduced amount of the KefB protein, as compared with an unmodified bacterium, or the modified bacterium is unable to synthesize the KefB protein. The phrase "bacterium has been modified to attenuate expression of the kefB gene" also means that the target gene is modified in such a way that the modified gene encodes a mutant KefB protein which has a decreased activity.

The phrase "inactivation of the kefb gene" means that the modified gene encodes a completely non-functional protein. It is also possible that the modified DNA region is unable to naturally express the gene due to the deletion of a part of the gene, the shifting of the reading frame of the gene, the introduction of missense/nonsense mutation(s), or the modification of an adjacent region of the gene, including sequences controlling gene expression, such as a promoter, enhancer, attenuator, ribosome-binding site, etc.

The kefB gene encodes the KefB protein, a potassium CPA2 transporter (synonyms—B3350, TrkB). The kefB gene of *E. coli* (nucleotide positions 3,478,629 to 3,476,824; GenBank accession no. NC_000913.2; gi:49175990; SEQ ID NO: 1) is located between the slyD and kefG genes on the chromosome of *E. coli* K-12. The nucleotide sequence of the kefB gene and the amino acid sequence of KefB encoded by the kefB gene are shown in SEQ ID NO: 1 and SEQ ID NO: 2, respectively.

Since there may be some differences in DNA sequences between the genera or strains of the Enterobacteriaceae family, the kefB gene to be inactivated on the chromosome is not limited to the gene shown in SEQ ID No: 1, but may include genes homologous to SEQ ID No: 1 encoding variants of the KefB protein. The phrase "variants" or "variant protein" as used in the present invention means a protein which has changes in the sequence, whether they are deletions, insertions, additions, or substitutions of amino acids, but still maintains the activity of the product as the KefB protein. The number of changes in the variant protein depends on the position or the type of amino acid residues in the three dimensional structure of the protein. It may be 1 to 30, preferably 1 to 15, and more preferably 1 to 5 in SEQ ID NO: 2. These changes in the variants can occur in regions of the protein which are not critical for the function of the protein. This is because some amino acids have high homology to one another so the three dimensional structure or activity is not affected by such a change. These changes in the variant protein can occur in regions of the protein which are not critical for the function of the protein. Therefore, the protein variant encoded by the kefB gene may have a homology of not less than 80%, preferably not less than 90%, and most preferably not less than 95%, with respect to the entire amino acid sequence shown in SEQ ID NO. 2, as long as the ability of the KefB protein to cause efflux of potassium prior to inactivation is maintained.

Homology between two amino acid sequences can be determined using well-known methods, for example, the computer program BLAST 2.0, which calculates three parameters: score, identity and similarity.

Moreover, the kefb gene may be a variant which hybridizes under stringent conditions with the nucleotide sequence shown in SEQ ID NO: 1, or a probe which can be prepared from the nucleotide sequence under stringent conditions, provided that it encodes a functional KefB protein prior to inactivation. "Stringent conditions" include those under which a specific hybrid, for example, a hybrid having homology of not less than 60%, preferably not less than 70%, more preferably not less than 80%, still more preferably not less than 90%, and most preferably not less than 95%, is formed and a non-specific hybrid, for example, a hybrid having homology lower than the above, is not formed. For example, stringent conditions are exemplified by washing one time or more, preferably two or three times, at a salt concentration of 1×SSC, 0.1% SDS, preferably 0.1×SSC, 0.1% SDS at 60° C. Duration of washing depends on the type of membrane used for blotting and, as a rule, may be what is recommended by the manufacturer. For example, the recommended duration of washing for the Hybond™ N+ nylon membrane (Amersham) under stringent conditions is 15 minutes. Preferably, washing may be performed 2 to 3 times. The length of the probe may be suitably selected, depending on the hybridization conditions, and usually varies from 100 bp to 1 kbp.

Expression of the kefB gene can be attenuated by introducing a mutation into the gene on the chromosome so that intracellular activity of the protein encoded by the gene is decreased as compared with an unmodified strain. Such a mutation on the gene can be replacement of one base or more to cause an amino acid substitution in the protein encoded by the gene (missense mutation), introduction of a stop codon (nonsense mutation), deletion of one or two bases to cause a frame shift, insertion of a drug-resistance gene, or deletion of a part of the gene or the entire gene (Qiu, Z. and Goodman, M. F., J. Biol. Chem., 272, 8611-8617 (1997); Kwon, D. H. et al, J. Antimicrob. Chemother., 46, 793-796 (2000)). Expression of the kefB gene can also be attenuated by modifying an expression regulating sequence such as the promoter, the Shine-Dalgarno (SD) sequence, etc. (WO95/34672, Carrier, T. A. and Keasling, J. D., Biotechnol Prog 15, 58-64 (1999)).

For example, the following methods may be employed to introduce a mutation by gene recombination. A mutant gene encoding a mutant protein having a decreased activity is prepared, and a bacterium to be modified is transformed with a DNA fragment containing the mutant gene. Then the native gene on the chromosome is replaced with the mutant gene by homologous recombination, and the resulting strain is selected. Such gene replacement using homologous recombination can be conducted by the method employing a linear DNA, which is known as "Red-driven integration" (Datsenko, K. A. and Wanner, B. L., Proc. Natl. Acad. Sci. USA, 97, 12, p 6640-6645 (2000)), or by methods employing a plasmid containing a temperature-sensitive replication (U.S. Pat. No. 6,303,383 or JP 05-007491A). Furthermore, the incorporation of a site-specific mutation by gene substitution using homologous recombination such as set forth above can also be conducted with a plasmid lacking the ability to replicate in the host.

Expression of the gene can also be attenuated by insertion of a transposon or an IS factor into the coding region of the gene (U.S. Pat. No. 5,175,107), or by conventional methods, such as mutagenesis treatment using UV irradiation or nitrosoguanidine (N-methyl-N'-nitro-N-nitrosoguanidine) treatment.

The presence of activity of the KefB protein can be detected by complementation of mutation kefB⁻ by the method described, for example, in Ness, L. S. and Booth, I. R., J. Biol. Chem., 1999, 274 (14):9524-9530. Thus, reduced or absent activity of the KefB protein in the bacterium according to the present invention can be determined when compared to the parent unmodified bacterium.

The presence or absence of the kefB gene on the chromosome of a bacterium can be detected by well-known methods, including PCR, Southern blotting, and the like. In addition, the level of gene expression can be estimated by measuring the amount of mRNA transcribed from the gene using various well-known methods, including Northern blotting, quantitative RT-PCR, and the like. The amount or molecular weight of the protein encoded by the gene can be measured by well-known methods, including SDS-PAGE followed by immuno-blotting assay (Western blotting analysis) and the like.

Methods for preparation of plasmid DNA, digestion and ligation of DNA, transformation, selection of an oligonucleotide as a primer, and the like may be ordinary methods well-known to one skilled in the art. These methods are described, for instance, in Sambrook, J., Fritsch, E. F., and Maniatis, T., "Molecular Cloning: A Laboratory Manual, Second Edition", Cold Spring Harbor Laboratory Press (1989).

L-Amino Acid-Producing Bacteria

As a bacterium of the present invention which is modified to attenuate expression of the kefb gene, bacteria which are able to produce either an aromatic or a non-aromatic L-amino acid may be used.

The bacterium of the present invention can be obtained by attenuating expression of the kefb gene in a bacterium which inherently has the ability to produce an L-amino acid. Alternatively, the bacterium of present invention can be obtained by imparting the ability to produce an L-amino acid to a bacterium already having attenuated expression of the kefB gene.

L-Threonine-Producing Bacteria

Examples of parent strains for deriving the L-threonine-producing bacteria of the present invention include, but are not limited to, strains belonging to the genus Escherichia, such as E. coli TDH-6/pVIC40 (VKPM B-3996) (U.S. Pat. No. 5,175,107, U.S. Pat. No. 5,705,371), E. coli 472T23/pYN7 (ATCC 98081) (U.S. Pat. No. 5,631,157), E. coli NRRL-21593 (U.S. Pat. No. 5,939,307), E. coli FERM BP-3756 (U.S. Pat. No. 5,474,918), E. coli FERM BP-3519 and FERM BP-3520 (U.S. Pat. No. 5,376,538), E. coli MG442 (Gusyatiner et al., Genetika (in Russian), 14, 947-956 (1978)), E. coli VL643 and VL2055 (EP 1149911 A), and the like.

The strain TDH-6 is deficient in the thrC gene, as well as being sucrose-assimilative, and the ilvA gene has a leaky mutation. This strain also has a mutation in the rhtA gene, which imparts resistance to high concentrations of threonine or homoserine. The strain B-3996 contains the plasmid pVIC40 which was obtained by inserting a thrA*BC operon which includes a mutant thrA gene into a RSF1010-derived vector. This mutant thrA gene encodes aspartokinase homoserine dehydrogenase I which has substantially desensitized feedback inhibition by threonine. The strain B-3996 was deposited on Nov. 19, 1987 in the All-Union Scientific Center of Antibiotics (Nagatinskaya Street 3-A, 117105 Moscow, Russian Federation) under the accession number RIA 1867. The strain was also deposited in the Russian National Collection of Industrial Microorganisms (VKPM) (Russia, 117545 Moscow, 1 Dorozhny proezd. 1) on Apr. 7, 1987 under the accession number VKPM B-3996.

E. coli VKPM B-5318 (EP 0593792B) may also be used as a parent strain for deriving L-threonine-producing bacteria of the present invention. The strain B-5318 is prototrophic with regard to isoleucine, and a temperature-sensitive lambda-phage C1 repressor and PR promoter replaces the regulatory region of the threonine operon in plasmid pVIC40. The strain VKPM B-5318 was deposited in the Russian National Collection of Industrial Microorganisms (VKPM) on May 3, 1990 under accession number of VKPM B-5318.

Preferably, the bacterium of the present invention is additionally modified to enhance expression of one or more of the following genes:

the mutant thrA gene which codes for aspartokinase homoserine dehydrogenase I resistant to feed back inhibition by threonine;

the thrB gene which codes for homoserine kinase;

the thrC gene which codes for threonine synthase;

the rhtA gene which codes for a putative transmembrane protein;

the asd gene which codes for aspartate-β-semialdehyde dehydrogenase; and the aspC gene which codes for aspartate aminotransferase (aspartate transaminase);

The thrA gene which encodes aspartokinase homoserine dehydrogenase I of *Escherichia coli* has been elucidated (nucleotide positions 337 to 2799, GenBank accession NC_000913.2, gi: 49175990). The thrA gene is located between the thrL and thrB genes on the chromosome of *E. coli* K-12. The thrB gene which encodes homoserine kinase of *Escherichia coli* has been elucidated (nucleotide positions 2801 to 3733, GenBank accession NC_000913.2, gi: 49175990). The thrB gene is located between the thrA and thrC genes on the chromosome of *E. coli* K-12. The thrC gene which encodes threonine synthase of *Escherichia coli* has been elucidated (nucleotide positions 3734 to 5020, GenBank accession NC_000913.2, gi: 49175990). The thrC gene is located between the thrB gene and the yaaX open reading frame on the chromosome of *E. coli* K-12. All three genes functions as a single threonine operon. To enhance expression of the threonine operon, the attenuator region which affects the transcription is desirably removed from the operon (WO2005/049808, WO2003/097839).

A mutant thrA gene which codes for aspartokinase homoserine dehydrogenase I resistant to feed back inhibition by threonine, as well as, the thrB and thrC genes can be obtained as one operon from the well-known plasmid pVIC40 which is present in the threonine producing *E. coli* strain VKPM B-3996. Plasmid pVIC40 is described in detail in U.S. Pat. No. 5,705,371.

The rhtA gene is present at 18 min on the *E. coli* chromosome close to the glnHPQ operon, which encodes components of the glutamine transport system. The rhtA gene is identical to ORF1 (ybiF gene, nucleotide positions 764 to 1651, GenBank accession number AAA218541, gi:440181) and is located between the pexB and ompX genes. The unit expressing a protein encoded by the ORF1 has been designated the rhtA gene (rht: resistance to homoserine and threonine). Also, it was revealed that the rhtA23 mutation is an A-for-G substitution at position −1 with respect to the ATG start codon (ABSTRACTS of the 17th International Congress of Biochemistry and Molecular Biology in conjugation with Annual Meeting of the American Society for Biochemistry and Molecular Biology, San Francisco, Calif. Aug. 24-29, 1997, abstract No. 457, EP 1013765 A).

The asd gene of *E. coli* has already been elucidated (nucleotide positions 3572511 to 3571408, GenBank accession NC_000913.1, gi:16131307), and can be obtained by PCR (polymerase chain reaction; refer to White, T. J. et al., Trends Genet., 5, 185 (1989)) utilizing primers prepared based on the nucleotide sequence of the gene. The asd genes of other microorganisms can be obtained in a similar manner.

Also, the aspC gene of *E. coli* has already been elucidated (nucleotide positions 983742 to 984932, GenBank accession NC_000913.1, gi:16128895), and can be obtained by PCR. The aspC genes of other microorganisms can be obtained in a similar manner.

L-Lysine-Producing Bacteria

Examples of L-lysine-producing bacteria belonging to the genus *Escherichia* include mutants having resistance to an L-lysine analogue. The L-lysine analogue inhibits growth of bacteria belonging to the genus *Escherichia*, but this inhibition is fully or partially desensitized when L-lysine coexists in a medium. Examples of the L-lysine analogue include, but are not limited to, oxalysine, lysine hydroxamate, S-(2-aminoethyl)-L-cysteine (AEC), γ-methyllysine, α-chlorocaprolactam and so forth. Mutants having resistance to these lysine analogues can be obtained by subjecting bacteria belonging to the genus *Escherichia* to a conventional artificial mutagenesis treatment. Specific examples of bacterial strains useful for producing L-lysine include *Escherichia coli* AJ11442 (FERM BP-1543, NRRL B-12185; see U.S. Pat. No. 4,346,170) and *Escherichia coli* VL611. In these microorganisms, feedback inhibition of aspartokinase by L-lysine is desensitized.

The strain WC196 may be used as an L-lysine producing bacterium of *Escherichia coli*. This bacterial strain was bred by conferring AEC resistance to the strain W3110, which was derived from *Escherichia coli* K-12. The resulting strain was designated *Escherichia coli* AJ13069 and was deposited at the National Institute of Bioscience and Human-Technology, Agency of Industrial Science and Technology (currently National Institute of Advanced Industrial Science and Technology, International Patent Organism Depositary, Tsukuba Central 6, 1-1, Higashi 1-Chome, Tsukuba-shi, Ibaraki-ken, 305-8566, Japan) on Dec. 6, 1994 and received an accession number of FERM P-14690. Then, it was converted to an international deposit under the provisions of the Budapest Treaty on Sep. 29, 1995, and received an accession number of FERM BP-5252 (U.S. Pat. No. 5,827,698).

Examples of parent strains for deriving L-lysine-producing bacteria of the present invention also include strains in which expression of one or more genes encoding an L-lysine biosynthetic enzyme are enhanced. Examples of such genes include, but are not limited to, genes encoding dihydrodipicolinate synthase (dapA), aspartokinase (lysC), dihydrodipicolinate reductase (dapB), diaminopimelate decarboxylase (lysA), diaminopimelate dehydrogenase (ddh) (U.S. Pat. No. 6,040,160), phosphoenolpyrvate carboxylase (ppc), aspartate semialdehyde dehydrogenease (asd), and aspartase (aspA) (EP 1253195 A). In addition, the parent strains may have an increased level of expression of the gene involved in energy efficiency (cyo) (EP 1170376 A), the gene encoding nicotinamide nucleotide transhydrogenase (pntAB) (U.S. Pat. No. 5,830,716), the ybjE gene (WO2005/073390), or combinations thereof.

Examples of parent strains for deriving L-lysine-producing bacteria of the present invention also include strains having decreased or eliminated activity of an enzyme that catalyzes a reaction for generating a compound other than L-lysine by branching off from the biosynthetic pathway of L-lysine. Examples of the enzymes that catalyze a reaction for generating a compound other than L-lysine by branching off from the biosynthetic pathway of L-lysine include homoserine dehydrogenase, lysine decarboxylase (U.S. Pat. No. 5,827,698), and the malic enzyme (WO2005/010175).

L-Cysteine-Producing Bacteria

Examples of parent strains for deriving L-cysteine-producing bacteria of the present invention include, but are not limited to, strains belonging to the genus *Escherichia*, such as *E. coli* JM15 which is transformed with different cysE alleles coding for feedback-resistant serine acetyltransferases (U.S. Pat. No. 6,218,168, Russian patent application 2003121601); *E. coli* W3110 having over-expressed genes which encode proteins suitable for secreting substances toxic for cells (U.S. Pat. No. 5,972,663); *E. coli* strains having lowered cysteine desulfohydrase activity (JP11155571A2); *E. coli* W3110 with increased activity of a positive transcriptional regulator for cysteine regulon encoded by the cysB gene (WO0127307A1), and the like.

L-Leucine-Producing Bacteria

Examples of parent strains for deriving L-leucine-producing bacteria of the present invention include, but are not limited to, strains belonging to the genus *Escherichia*, such as *E. coli* strains resistant to leucine (for example, the strain 57 (VKPM B-7386, U.S. Pat. No. 6,124,121)) or leucine analogs including β-2-thienylalanine, 3-hydroxyleucine, 4-azaleucine, 5,5,5-trifluoroleucine (JP 62-34397 B and JP 8-70879 A); *E. coli* strains obtained by the gene engineering method described in WO96/06926; *E. coli* H-9068 (JP 8-70879 A), and the like.

The bacterium of the present invention may be improved by enhancing the expression of one or more genes involved in L-leucine biosynthesis. Examples include genes of the leuABCD operon, which are preferably represented by a mutant leuA gene coding for isopropylmalate synthase freed from feedback inhibition by L-leucine (U.S. Pat. No. 6,403,342). In addition, the bacterium of the present invention may be improved by enhancing the expression of one or more genes coding for proteins which excrete L-amino acid from the bacterial cell. Examples of such genes include the b2682 and b2683 genes (ygaZH genes) (EP 1239041 A2).

L-Histidine-Producing Bacteria

Examples of parent strains for deriving L-histidine-producing bacteria of the present invention include, but are not limited to, strains belonging to the genus *Escherichia*, such as *E. coli* strain 24 (VKPM B-5945, RU2003677); *E. coli* strain 80 (VKPM B-7270, RU2119536); *E. coli* NRRL B-12116-B12121 (U.S. Pat. No. 4,388,405); *E. coli* H-9342 (FERM BP-6675) and H-9343 (FERM BP-6676) (U.S. Pat. No. 6,344,347); *E. coli* H-9341 (FERM BP-6674) (EP1085087); *E. coli* AI80/pFM201 (U.S. Pat. No. 6,258,554) and the like.

Examples of parent strains for deriving L-histidine-producing bacteria of the present invention also include strains in which expression of one or more genes encoding an L-histidine biosynthetic enzyme are enhanced. Examples of such genes include genes encoding ATP phosphoribosyltransferase (hisG), phosphoribosyl AMP cyclohydrolase (hisI), phosphoribosyl-ATP pyrophosphohydrolase (hisIE), phosphoribosylformimino-5-aminoimidazole carboxamide ribotide isomerase (hisA), amidotransferase (hisH), histidinol phosphate aminotransferase (hisC), histidinol phosphatase (hisB), histidinol dehydrogenase (hisD), and so forth.

It is known that the L-histidine biosynthetic enzymes encoded by hisG and hisBHAFI are inhibited by L-histidine, and therefore an L-histidine-producing ability can also be efficiently enhanced by introducing a mutation conferring resistance to the feedback inhibition into ATP phosphoribosyltransferase (Russian Patent Nos. 2003677 and 2119536).

Specific examples of strains having an L-histidine-producing ability include *E. coli* FERM-P 5038 and 5048 which have been introduced with a vector carrying a DNA encoding an L-histidine-biosynthetic enzyme (JP 56-005099 A), *E. coli* strains introduced with rht, a gene for an amino acid-export (EP1016710A), *E. coli* 80 strain imparted with sulfaguanidine, DL-1,2,4-triazole-3-alanine, and streptomycin-resistance (VKPM B-7270, Russian Patent No. 2119536), and so forth.

L-Glutamic Acid-Producing Bacteria

Examples of parent strains for deriving L-glutamic acid-producing bacteria of the present invention include, but are not limited to, strains belonging to the genus *Escherichia*, such as *E. coli* VL334thrC+ (EP 1172433). *E. coli* VL334 (VKPM B-1641) is an L-isoleucine and L-threonine auxotrophic strain having mutations in thrC and ilvA genes (U.S. Pat. No. 4,278,765). A wild-type allele of the thrC gene was transferred by the method of general transduction using a bacteriophage P1 grown on the wild-type *E. coli* strain K12 (VKPM B-7) cells. As a result, an L-isoleucine auxotrophic strain VL334thrC+ (VKPM B-8961), which is able to produce L-glutamic acid, was obtained.

Examples of parent strains for deriving the L-glutamic acid-producing bacteria of the present invention include, but are not limited to, strains in which expression of one or more genes encoding an L-glutamic acid biosynthetic enzyme are enhanced. Examples of such genes include genes encoding glutamate dehydrogenase (gdh), glutamine synthetase (glnA), glutamate synthetase (gltAB), isocitrate dehydrogenase (icdA), aconitate hydratase (acnA, acnB), citrate synthase (gltA), phosphoenolpyruvate carboxylase (ppc), pyruvate dehydrogenase (aceEF, lpdA), pyruvate kinase (pykA, pykF), phosphoenolpyruvate synthase (ppsA), enolase (eno), phosphoglyceromutase (pgmA, pgmI), phosphoglycerate kinase (pgk), glyceraldehyde-3-phosphate dehydrogenase (gapA), triose phosphate isomerase (tpiA), fructose bisphosphate aldolase (fbp), phosphofructokinase (pfkA, pfkB), and glucose phosphate isomerase (pgi).

Examples of strains modified so that expression of the citrate synthetase gene, the phosphoenolpyruvate carboxylase gene, and/or the glutamate dehydrogenase gene is/are enhanced include those disclosed in EP1078989A, EP955368A, and EP952221A.

Examples of parent strains for deriving the L-glutamic acid-producing bacteria of the present invention also include strains having decreased or eliminated activity of an enzyme that catalyzes synthesis of a compound other than L-glutamic acid by branching off from an L-glutamic acid biosynthesis pathway. Examples of such genes include genes encoding isocitrate lyase (aceA), α-ketoglutarate dehydrogenase (sucA), phosphotransacetylase (pta), acetate kinase (ack), acetohydroxy acid synthase (ilvG), acetolactate synthase (ilvI), formate acetyltransferase (pfl), lactate dehydrogenase (ldh), and glutamate decarboxylase (gadAB). Bacteria belonging to the genus *Escherichia* deficient in α-ketoglutarate dehydrogenase activity or having a reduced α-ketoglutarate dehydrogenase activity and methods for obtaining them are described in U.S. Pat. Nos. 5,378,616 and 5,573,945. Specifically, these strains include the following:

*E. coli* W3110sucA::Kmr
*E. coli* AJ12624 (FERM BP-3853)
*E. coli* AJ12628 (FERM BP-3854)
*E. coli* AJ12949 (FERM BP-4881)

*E. coli* W3110sucA::Kmr is obtained by disrupting the α-ketoglutarate dehydrogenase gene (hereinafter referred to as "sucA gene") of *E. coli* W3110. This strain is completely deficient in α-ketoglutarate dehydrogenase.

Other examples of L-glutamic acid-producing bacterium include those which belong to the genus *Escherichia* and have resistance to an aspartic acid antimetabolite. These strains can also be deficient in α-ketoglutarate dehydrogenase activity and include, for example, *E. coli* AJ13199 (FERM BP-5807) (U.S. Pat. No. 5,908,768), FFRM P-12379, which additionally has a low L-glutamic acid decomposing ability (U.S. Pat. No. 5,393,671); AJ13138 (FERM BP-5565) (U.S. Pat. No. 6,110,714), and the like.

Examples of L-glutamic acid-producing bacteria, include mutant strains belonging to the genus *Pantoea* which are deficient in α-ketoglutarate dehydrogenase activity or have a decreased α-ketoglutarate dehydrogenase activity, and can be obtained as described above. Such strains include *Pantoea ananatis* AJ13356. (U.S. Pat. No. 6,331,419). *Pantoea*

*ananatis* AJ13356 was deposited at the National Institute of Bioscience and Human-Technology, Agency of Industrial Science and Technology, Ministry of International Trade and Industry (currently, National Institute of Advanced Industrial Science and Technology, International Patent Organism Depositary, Central 6, 1-1, Higashi 1-Chome, Tsukuba-shi, Ibaraki-ken, 305-8566, Japan) on Feb. 19, 1998 under an accession number of FERM P-16645. It was then converted to an international deposit under the provisions of Budapest Treaty on Jan. 11, 1999 and received an accession number of FERM BP-6615. *Pantoea ananatis* AJ13356 is deficient in α-ketoglutarate dehydrogenase activity as a result of disruption of the αKGDH-E1 subunit gene (sucA). The above strain was identified as *Enterobacter agglomerans* when it was isolated and deposited as the *Enterobacter agglomerans* AJ13356. However, it was recently re-classified as *Pantoea ananatis* on the basis of nucleotide sequencing of 16S rRNA and so forth. Although AJ13356 was deposited at the aforementioned depository as *Enterobacter agglomerans*, for the purposes of this specification, they are described as *Pantoea ananatis*.

L-Phenylalanine-Producing Bacteria

Examples of parent strains for deriving L-phenylalanine-producing bacteria of the present invention include, but are not limited to, strains belonging to the genus *Escherichia*, such as *E. coli* AJ12739 (tyrA::Tn10, tyrR) (VKPM B-8197); *E. coli* HW1089 (ATCC 55371) harboring the mutant pheA34 gene (U.S. Pat. No. 5,354,672); *E. coli* MWEC101-b (KR8903681); *E. coli* NRRL B-12141, NRRL B-12145, NRRL B-12146 and NRRL B-12147 (U.S. Pat. No. 4,407,952). Also, as a parent strain, *E. coli* K-12 [W3110 (tyrA)/pPHAB (FERM BP-3566), *E. coli* K-12 [W3110 (tyrA)/pPHAD] (FERM BP-12659), *E. coli* K-12 [W3110 (tyrA)/pPHATerm] (FERM BP-12662) and *E. coli* K-12 [W3110 (tyrA)/pBR-aroG4, pACMAB] named as AJ 12604 (FERM BP-3579) may be used (EP 488424 B1). Furthermore, L-phenylalanine producing bacteria belonging to the genus *Escherichia* with an enhanced activity of the protein encoded by the yedA gene or the yddG gene may also be used (U.S. patent applications 2003/0148473 A1 and 2003/0157667 A1).

L-Tryptophan-Producing Bacteria

Examples of parent strains for deriving the L-tryptophan-producing bacteria of the present invention include, but are not limited to, strains belonging to the genus *Escherichia*, such as *E. coli* JP4735/pMU3028 (DSM10122) and JP6015/pMU91 (DSM10123) which is deficient in the tryptophanyl-tRNA synthetase encoded by mutant trpS gene (U.S. Pat. No. 5,756,345); *E. coli* SV164 (pGH5) having a serA allele encoding phosphoglycerate dehydrogenase free from feedback inhibition by serine and a trpE allele encoding anthranilate synthase free from feedback inhibition by tryptophan (U.S. Pat. No. 6,180,373); *E. coli* AGX17 (pGX44) (NRRL B-12263) and AGX6 (pGX50) aroP (NRRL B-12264) which is deficient in the enzyme tryptophanase (U.S. Pat. No. 4,371,614); *E. coli* AGX17/pGX50, pACKG4-pps in which a phosphoenolpyruvate-producing ability is enhanced (WO9708333, U.S. Pat. No. 6,319,696), and the like may be used. L-tryptophan-producing bacteria belonging to the genus *Escherichia* with an enhanced activity of the protein encoded by the yedA gene or the yddG gene may also be used (U.S. patent applications 2003/0148473 A1 and 2003/0157667 A1).

Examples of parent strains for deriving the L-tryptophan-producing bacteria of the present invention also include strains in which one or more activities of the enzymes selected from anthranilate synthase, phosphoglycerate dehydrogenase, and tryptophan synthase are enhanced. The anthranilate synthase and phosphoglycerate dehydrogenase are both subject to feedback inhibition by L-tryptophan and L-serine, so that a mutation desensitizing the feedback inhibition may be introduced into these enzymes. Specific examples of strains having such a mutation include a *E. coli* SV164 which harbors desensitized anthranilate synthase and a transformant strain obtained by introducing into the *E. coli* SV164 the plasmid pGH5 (WO 94/08031), which contains a mutant serA gene encoding feedback-desensitized phosphoglycerate dehydrogenase.

Examples of parent strains for deriving the L-tryptophan-producing bacteria of the present invention also include strains into which the tryptophan operon which contains a gene encoding desensitized anthranilate synthase has been introduced (JP 57-71397 A, JP 62-244382 A, U.S. Pat. No. 4,371,614). Moreover, L-tryptophan-producing ability may be imparted by enhancing expression of a gene which encodes tryptophan synthase, among tryptophan operons (trpBA). The tryptophan synthase consists of α and β subunits which are encoded by the trpA and trpB genes, respectively. In addition, L-tryptophan-producing ability may be improved by enhancing expression of the isocitrate lyase-malate synthase operon (WO2005/103275).

L-Proline-Producing Bacteria

Examples of parent strains for deriving L-proline-producing bacteria of the present invention include, but are not limited to, strains belonging to the genus *Escherichia*, such as *E. coli* 702ilvA (VKPM B-8012) which is deficient in the ilvA gene and is able to produce L-proline (EP 1172433). The bacterium of the present invention may be improved by enhancing the expression of one or more genes involved in L-proline biosynthesis. Examples of such genes for L-proline producing bacteria which are preferred include the proB gene coding for glutamate kinase of which feedback inhibition by L-proline is desensitized (DE Patent 3127361). In addition, the bacterium of the present invention may be improved by enhancing the expression of one or more genes coding for proteins excreting L-amino acid from bacterial cell. Such genes are exemplified by b2682 and b2683 genes (ygaZH genes) (EP1239041 A2).

Examples of bacteria belonging to the genus *Escherichia*, which have an activity to produce L-proline include the following *E. coli* strains: NRRL B-12403 and NRRL B-12404 (GB Patent 2075056), VKPM B-8012 (Russian patent application 2000124295), plasmid mutants described in DE Patent 3127361, plasmid mutants described by Bloom F. R. et al (The 15$^{th}$ Miami winter symposium, 1983, p. 34), and the like.

L-Arginine-Producing Bacteria

Examples of parent strains for deriving L-arginine-producing bacteria of the present invention include, but are not limited to, strains belonging to the genus *Escherichia*, such as *E. coli* strain 237 (VKPM B-7925) (U.S. Patent Application 2002/058315 A1) and its derivative strains harboring mutant N-acetylglutamate synthase (Russian Patent Application No. 2001112869), *E. coli* strain 382 (VKPM B-7926) (EP1170358A1), an arginine-producing strain into which argA gene encoding N-acetylglutamate synthetase is introduced therein (EP1170361A1), and the like.

Examples of parent strains for deriving L-arginine producing bacteria of the present invention also include strains in which expression of one or more genes encoding an L-arginine biosynthetic enzyme are enhanced. Examples of such genes include genes encoding N-acetylglutamyl phosphate reductase (argC), ornithine acetyl transferase (argJ), N-acetylglutamate kinase (argB), acetylornithine transaminase (argD), ornithine carbamoyl transferase (argF), argininosuccinic acid synthetase (argG), argininosuccinic acid lyase (argH), and carbamoyl phosphate synthetase (carAB).

L-Valine-Producing Bacteria

Example of parent strains for deriving L-valine-producing bacteria of the present invention include, but are not limited to, strains which have been modified to overexpress the ilvGMEDA operon (U.S. Pat. No. 5,998,178). It is desirable to remove the region of the ilvGMEDA operon which is required for attenuation so that expression of the operon is not attenuated by L-valine that is produced. Furthermore, the ilvA gene in the operon is desirably disrupted so that threonine deaminase activity is decreased.

Examples of parent strains for deriving L-valine-producing bacteria of the present invention include also include mutants having a mutation of amino-acyl t-RNA synthetase (U.S. Pat. No. 5,658,766). For example, *E. coli* VL1970, which has a mutation in the ileS gene encoding isoleucine tRNA synthetase, can be used. *E. coli* VL1970 has been deposited in the Russian National Collection of Industrial Microorganisms (VKPM) (Russia, 113545 Moscow, 1 Dorozhny Proezd, 1) on Jun. 24, 1988 under accession number VKPM B-4411.

Furthermore, mutants requiring lipoic acid for growth and/or lacking $H^+$-ATPase can also be used as parent strains (WO96/06926).

L-Isoleucine-Producing Bacteria

Examples of parent strains for deriving L-isoleucine producing bacteria of the present invention include, but are not limited to, mutants having resistance to 6-dimethylaminopurine (JP 5-304969 A), mutants having resistance to an isoleucine analogue such as thiaisoleucine and isoleucine hydroxamate, and mutants additionally having resistance to DL-ethionine and/or arginine hydroxamate (JP 5-130882 A). In addition, recombinant strains transformed with genes encoding proteins involved in L-isoleucine biosynthesis, such as threonine deaminase and acetohydroxate synthase, can also be used as parent strains (JP 2-458 A, FR 0356739, and U.S. Pat. No. 5,998,178).

2. Method of the Present Invention

The method of the present invention is a method for producing an L-amino acid comprising cultivating the bacterium of the present invention in a culture medium to produce and excrete the L-amino acid into the medium, and collecting the L-amino acid from the medium.

In the present invention, the cultivation, collection, and purification of an L-amino acid from the medium and the like may be performed in a manner similar to conventional fermentation methods wherein an amino acid is produced using a bacterium.

A medium used for culture may be either a synthetic or natural medium, so long as the medium includes a carbon source and a nitrogen source and minerals and, if necessary, appropriate amounts of nutrients which the bacterium requires for growth. The carbon source may include various carbohydrates such as glucose and sucrose, and various organic acids. Depending on the mode of assimilation of the chosen microorganism, alcohol, including ethanol and glycerol, may be used. As the nitrogen source, various ammonium salts such as ammonia and ammonium sulfate, other nitrogen compounds such as amines, a natural nitrogen source such as peptone, soybean-hydrolysate, and digested fermentative microorganism can be used. As minerals, potassium monophosphate, magnesium sulfate, sodium chloride, ferrous sulfate, manganese sulfate, calcium chloride, and the like can be used. As vitamins, thiamine, yeast extract, and the like, can be used.

The cultivation is preferably performed under aerobic conditions, such as a shaking culture, and a stirring culture with aeration, at a temperature of 20 to 40° C., preferably 30 to 38° C. The pH of the culture is usually between 5 and 9, preferably between 6.5 and 7.2. The pH of the culture can be adjusted with ammonia, calcium carbonate, various acids, various bases, and buffers. Usually, a 1 to 5-day cultivation leads to accumulation of the target L-amino acid in the liquid medium.

After cultivation, solids such as cells can be removed from the liquid medium by centrifugation or membrane filtration, and then the L-amino acid can be collected and purified by ion-exchange, concentration, and/or crystallization methods.

EXAMPLES

The present invention will be more concretely explained below with reference to the following non-limiting Examples.

Example 1

Construction of a Strain with an Inactivated kefB Gene

1. Deletion of the kefB Gene

A strain in which the kefB gene is deleted was constructed by the method initially developed by Datsenko, K. A. and Wanner, B. L. (Proc. Natl. Acad. Sci. USA, 2000, 97 (12): 6640-6645) called "Red-driven integration". According to this procedure, the PCR primers kefBL (SEQ ID NO: 3) and kefBR (SEQ ID NO: 4), which are homologous to both the regions adjacent to the kefB gene and the gene conferring antibiotic resistance, respectively, in the template plasmid, were constructed. The plasmid pACYC184 (NBL Gene Sciences Ltd., UK) (GenBank/EMBL accession no. X06403) was used as a template in the PCR reaction. Conditions for PCR were as follows: denaturation step: 3 min at 95° C.; profile for two first cycles: 1 min at 95° C., 30 sec at 50° C., 40 sec at 72° C.; profile for the last 25 cycles: 30 sec at 95° C., 30 sec at 54° C., 40 sec at 72° C.; final step: 5 min at 72° C.

A 1152 bp PCR product (FIG. 1) was obtained and purified in agarose gel and was used for electroporation of *E. coli* MG1655 (ATCC 700926), which contains the plasmid pKD46 having a temperature-sensitive replication. The plasmid pKD46 (Datsenko, K. A. and Wanner, B. L., Proc. Natl. Acad. Sci. USA, 2000, 97 (12):6640-6645) includes a 2,154-nucleotide DNA fragment of phage λ (nucleotide positions 31088 to 33241, GenBank accession no. J02459), and contains genes of the λ Red homologous recombination system (γ, β, exo genes) under the control of the arabinose-inducible $P_{araB}$ promoter. The plasmid pKD46 is necessary for integration of the PCR product into the chromosome of strain MG1655. The strain MG1655 can be obtained from American Type Culture Collection. (P.O. Box 1549 Manassas, Va. 20108, United States of America).

Electrocompetent cells were prepared as follows: *E. coli* MG1655/pKD46 was grown overnight at 30° C. in LB medium containing ampicillin (100 mg/l), and the culture was diluted 100 times with 5 ml of SOB medium (Sambrook et al, "Molecular Cloning: A Laboratory Manual, Second Edition", Cold Spring Harbor Laboratory Press, 1989) with ampicillin and L-arabinose (1 mM). The cells were grown with aeration at 30° C. to an $OD_{600}$ of ≈0.6 and then were made electrocompetent by 100-fold concentrating and washing three times with ice-cold deionized $H_2O$. Electroporation was performed using 70 µl of cells and ≈100 ng of the PCR product.

Cells after electroporation were incubated with 1 ml of SOC medium (Sambrook et al, "Molecular Cloning: A Laboratory Manual, Second Edition", Cold Spring Harbor Laboratory Press, 1989) at 37° C. for 2.5 hours and then were plated onto L-agar containing chloramphenicol (30 µg/ml) and were grown at 37° C. to select Cm$^R$ recombinants. Then, to eliminate the pKD46 plasmid, 2 passages on L-agar with Cm at 42° C. were performed and the obtained colonies were tested for sensitivity to ampicillin.

2. Verification of the kefB Gene Deletion by PCR

Figure 2:
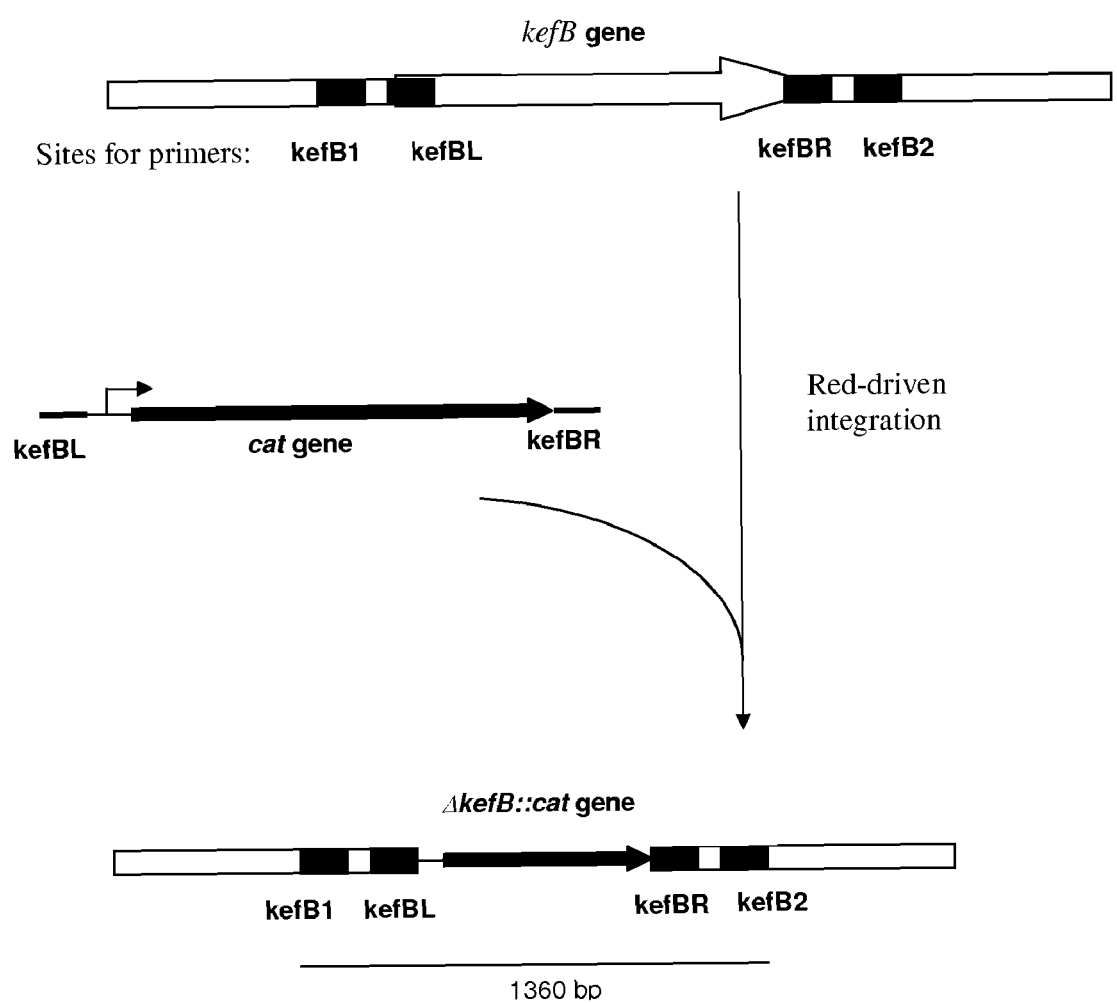
FIG. 2 shows the construction of the chromosomal DNA fragment containing the inactivated kefB gene.

The mutants having the kefB gene deleted and marked with the Cm resistance gene were verified by PCR. Locus-specific primers kefB1 (SEQ ID NO: 5) and kefB2 (SEQ ID NO: 6) were used in PCR for the verification. Conditions for PCR verification were as follows: denaturation step: 3 min at 94° C.; profile for the 30 cycles: 30 sec at 94° C., 30 sec at 54° C., 1 min at 72° C.; final step: 7 min at 72° C. The PCR product obtained in the reaction with the parental kefB$^+$ strain MG1655 as the template was 2086 bp in length. The PCR product obtained in the reaction with the mutant strain as the template was 1360 bp in length (FIG. 2). The mutant strain was named MG1655 ΔkefB::cat Example 2

Production of L-Threonine by E. coli B-3996-ΔkefB

To test the effect of inactivation of the kefB gene on threonine production, DNA fragments from the chromosome of the above-described E. coli strain MG1655 ΔkefB::cat were transferred to the threonine-producing E. coli strain VKPM B-3996 by P1 transduction (Miller, J. H. Experiments in Molecular Genetics, Cold Spring Harbor Lab. Press, 1972, Plainview, N.Y.) to obtain the strain B-3996-ΔkefB.

Both E. coli strains, B-3996 and B-3996-ΔkefB, were grown for 18-24 hours at 37° C. on L-agar plates. To obtain a seed culture, the strains were grown on a rotary shaker (250 rpm) at 32° C. for 18 hours in 20×200-mm test tubes containing 2 ml of L-broth supplemented with 4% glucose. Then, the fermentation medium was inoculated with 0.21 ml (10%) seed material. The fermentation was performed in 2 ml of minimal medium for fermentation in 20×200-mm test tubes. Cells were grown for 65 hours at 32° C. with shaking at 250 rpm.

After cultivation, the amount of L-threonine, which had accumulated in the medium, was determined by paper chromatography using the following mobile phase: butanol-acetic acid-water=4:1:1 (v/v). A solution of ninhydrin (2%) in acetone was used as a visualizing reagent. A spot containing L-threonine was cut out, L-threonine was eluted with 0.5% water solution of CdCl$_2$, and the amount of L-threonine was estimated spectrophotometrically at 540 nm. The results of ten independent test tube fermentations are shown in Table 1.

The composition of the fermentation medium (g/l) was as follows:

| | |
|---|---|
| Glucose | 80.0 |
| (NH$_4$)$_2$SO$_4$ | 22.0 |
| NaCl | 0.8 |
| KH$_2$PO$_4$ | 2.0 |
| MgSO$_4$•7H$_2$O | 0.8 |
| FeSO$_4$•7H$_2$O | 0.02 |
| MnSO$_4$•5H$_2$O | 0.02 |
| Thiamine HCl | 0.0002 |
| Yeast extract | 1.0 |
| CaCO$_3$ | 30.0 |

Glucose and magnesium sulfate were sterilized separately. CaCO$_3$ was sterilized by dry-heat at 180° C. for 2 hours. The pH was adjusted to 7.0. The antibiotic was introduced into the medium after sterilization.

TABLE 1

| Strain | OD$_{540}$ | Amount of L-threonine, g/l |
|---|---|---|
| B-3996 | 19.6 ± 0.7 | 23.6 ± 0.3 |
| B-3996-ΔkefB | 20.4 ± 0.6 | 24.9 ± 1.0 |

As follows from Table 1, B-3996-ΔkefB produced a higher amount of L-threonine, as compared with B-3996.

Example 3

Production of L-Lysine by E. coli Strain WC196-ΔkefB

To test the effect of inactivation of the kefB gene on lysine production, DNA fragments from the chromosome of the above-described E. coli strain MG1655 ΔkefB::cat were transferred to the lysine-producing E. coli strain WC196 (FERM BP-5252) by P1 transduction (Miller, J. H. Experiments in Molecular Genetics, Cold Spring Harbor Lab. Press, 1972, Plainview, N.Y.) to obtain strain WC196-ΔkefB.

Both E. coli strains, WC196 and WC196-ΔkefB, were grown on a rotary shaker (250 rpm) at 32° C. for 18 hours in 20×200-mm test tubes containing 2 ml of medium diluted two times compared to the fermentation medium described below. Then 0.21 ml (10%) of the seed culture was inoculated into 2 ml of the fermentation medium in 20×200 mm test tubes. The fermentation was performed at 32° C. for 24 hours with shaking at 250 rpm.

After cultivation, the amount of L-lysine which had accumulated in the medium was determined by paper chromatography using the following mobile phase: butanol-acetic acid-water=4:1:1 (v/v). A solution of ninhydrin (2%) in acetone was used as a visualizing reagent. A spot containing L-lysine was cut out, L-lysine was eluted with 0.5% water solution of CdCl$_2$, and the amount of L-lysine was estimated spectrophotometrically at 540 nm. The results of five independent test-tube fermentations are shown in Table 2.

The composition of the fermentation medium (g/l) was as follows:

| | |
|---|---|
| Glucose | 40.0 |
| (NH$_4$)$_2$SO$_4$ | 24.0 |
| KH$_2$PO$_4$ | 1.0 |
| MgSO$_4$•7H$_2$O | 1.0 |
| FeSO$_4$•7H$_2$O | 0.01 |
| MnSO$_4$•5H$_2$O | 0.01 |
| Yeast extract | 2.0 |
| CaCO$_3$ | 30.0 |

Glucose, potassium phosphate and magnesium sulfate were sterilized separately. CaCO$_3$ was sterilized by dry-heat at 180° C. for 2 hours. The pH was adjusted to 7.0.

TABLE 2

| Strain | OD$_{540}$ | Amount of L-lysine, g/l |
|---|---|---|
| WC196 | 26.2 ± 0.5 | 2.1 ± 0.1 |
| WC196-ΔkefB | 28.6 ± 1.1 | 2.4 ± 0.1 |

As follows from Table 2, WC196-ΔkefB produced a higher amount of L-lysine, as compared with WC196.

Example 4

Production of L-Cysteine by *E. coli* JM15(ydeD)-ΔkefB

To test the effect of inactivation of the kefB gene on L-cysteine production, DNA fragments from the chromosome of the above-described *E. coli* strain MG1655 ΔkefB::cat can be transferred to the L-cysteine-producing *E. coli* strain JM15 (ydeD) by P1 transduction (Miller, J. H. Experiments in Molecular Genetics, Cold Spring Harbor Lab. Press, 1972, Plainview, N.Y.) to obtain the strain JM15(ydeD)-ΔkefB.

*E. coli* JM15(ydeD) is a derivative of *E. coli* JM15 (U.S. Pat. No. 6,218,168), which can be transformed with DNA having the ydeD gene encoding a membrane protein, and is not involved in a biosynthetic pathway of any L-amino acid (U.S. Pat. No. 5,972,663). The strain JM15 (CGSC#5042) can be obtained from The Coli Genetic Stock Collection at the *E. coli* Genetic Resource Center, MCD Biology Department, Yale University (cgsc.biology.yale.edu/).

Fermentation conditions for evaluation of L-cysteine production were described in detail in Example 6 of U.S. Pat. No. 6,218,168.

Example 5

Production of L-Leucine by *E. coli* 57-ΔkefB

To test the effect of inactivation of the kefB gene on L-leucine production, DNA fragments from the chromosome of the above-described *E. coli* strain MG1655 ΔkefB::cat can be transferred to the L-leucine-producing *E. coli* strain 57 (VKPM B-7386, U.S. Pat. No. 6,124,121) by P1 transduction (Miller, J. H. Experiments in Molecular Genetics, Cold Spring Harbor Lab. Press, 1972, Plainview, N.Y.) to obtain the strain 57-ΔkefB. The strain 57 has been deposited in the Russian National Collection of Industrial Microorganisms (VKPM) (Russia, 117545 Moscow, 1 Dorozhny proezd, 1) on May 19, 1997 under accession number VKPM B-7386.

Both *E. coli* strains, 57 and 57-ΔkefB, can be cultured for 18-24 hours at 37° C. on L-agar plates. To obtain a seed culture, the strains can be grown on a rotary shaker (250 rpm) at 32° C. for 18 hours in 20×200-mm test tubes containing 2 ml of L-broth supplemented with 4% sucrose. Then, the fermentation medium can be inoculated with 0.21 ml of seed material (10%). The fermentation can be performed in 2 ml of a minimal fermentation medium in 20×200-mm test tubes. Cells can be grown for 48-72 hours at 32° C. with shaking at 250 rpm. The amount of L-leucine can be measured by paper chromatography (liquid phase composition: butanol-acetic acid-water=4:1:1)

The composition of the fermentation medium (g/l) is as follows (pH 7.2):

| | |
|---|---|
| Glucose | 60.0 |
| $(NH_4)_2SO_4$ | 25.0 |
| $K_2HPO_4$ | 2.0 |
| $MgSO_4 \cdot 7H_2O$ | 1.0 |
| Thiamine | 0.01 |
| $CaCO_3$ | 25.0 |

Glucose and $CaCO_3$ are sterilized separately.

Example 6

Production of L-Histidine by *E. coli* Strain 80-ΔkefB

To test the effect of inactivation of the kefB gene on L-histidine production, DNA fragments from the chromosome of the above-described *E. coli* strain MG1655 ΔkefB::cat can be transferred to the histidine-producing *E. coli* strain 80 by P1 transduction (Miller, J. H. Experiments in Molecular Genetics, Cold Spring Harbor Lab. Press, 1972, Plainview, N.Y.) to obtain strain 80-ΔkefB. The strain 80 has been described in Russian patent 2119536 and deposited in the Russian National Collection of Industrial Microorganisms (Russia, 117545 Moscow, 1 Dorozhny proezd, 1) on Oct. 15, 1999 under accession number VKPM B-7270 and then converted to a deposit under the Budapest Treaty on Jul. 12, 2004.

Both *E. coli* strains, 80 and 80-ΔkefB, can be cultured in L-broth for 6 hours at 29° C. Then, 0.1 ml of obtained cultures can each be inoculated into 2 ml of fermentation medium in a 20×200-mm test tube and cultivated for 65 hours at 29° C. with shaking on a rotary shaker (350 rpm). After cultivation, the amount of histidine which accumulates in the medium can be determined by paper chromatography. The paper can be developed with a mobile phase consisting of n-butanol:acetic acid:water=4:1:1 (v/v). A solution of ninhydrin (0.5%) in acetone can be used as a visualizing reagent.

The composition of the fermentation medium (pH 6.0) is as follows (g/l):

| | |
|---|---|
| Glucose | 100.0 |
| Mameno (soybean hydrolysate) | 0.2 of as total nitrogen |
| L-proline | 1.0 |
| $(NH_4)_2SO_4$ | 25.0 |
| $KH_2PO_4$ | 2.0 |
| $MgSO_4 \cdot 7H_2O$ | 1.0 |
| $FeSO_4 \cdot 7H_2O$ | 0.01 |
| $MnSO_4$ | 0.01 |
| Thiamine | 0.001 |
| Betaine | 2.0 |
| $CaCO_3$ | 60.0 |

Glucose, proline, betaine and $CaCO_3$ are sterilized separately. The pH is adjusted to 6.0 before sterilization.

Example 7

Production of L-Glutamate by *E. coli* VL334thrC$^+$-ΔkefB

To test the effect of inactivation of the kefB gene on L-glutamate production, DNA fragments from the chromosome of the above-described *E. coli* strain MG1655 ΔkefB::cat can be transferred to the L-glutamate-producing *E. coli* strain VL334thrC$^+$ (EP 1172433) by P1 transduction (Miller, J. H. Experiments in Molecular Genetics, Cold Spring Harbor Lab. Press, 1972, Plainview, N.Y.) to obtain the strain VL334thrC$^+$-ΔkefB. The strain VL334thrC$^+$ has been deposited in the Russian National Collection of Industrial Microorganisms (VKPM) (Russia, 117545 Moscow, 1 Dorozhny proezd, 1) on Dec. 6, 2004 under the accession number VKPM B-8961 and then converted to a deposit under the Budapest Treaty on Dec. 8, 2004.

Both *E. coli* strains, VL334thrC$^+$ and VL334thrC$^+$-ΔkefB, can be grown for 18-24 hours at 37° C. on L-agar plates. Then, one loop of the cells can be transferred to test tubes containing 2 ml of fermentation medium. The fermentation medium contains glucose (60 g/l), ammonium sulfate (25 g/l), $KH_2PO_4$ (2 g/l), $MgSO_4$ (1 g/l), thiamine (0.1 mg/ml), L-isoleucine (70 µg/ml), and $CaCO_3$ (25 g/l). The pH should be adjusted to 7.2. Glucose and $CaCO_3$ are sterilized separately. Cultivation can be carried out at 30° C. for 3 days with shaking. After the cultivation, the amount of L-glutamic acid produced can be determined by paper chromatography (liquid phase composition of butanol-acetic acid-water=4:1:1) with subsequent staining by ninhydrin (1% solution in acetone) and further elution of the compounds in 50% ethanol with 0.5% $CdCl_2$.

Example 8

Production of L-Phenylalanine by *E. coli* AJ12739-ΔkefB

To test the effect of inactivation of the kefB gene on L-phenylalanine production, DNA fragments from the chromosome of the above-described *E. coli* strain MG1655 ΔkefB::cat can be transferred to the phenylalanine-producing *E. coli* strain AJ12739 by P1 transduction (Miller, J. H. Experiments in Molecular Genetics, Cold Spring Harbor Lab. Press, 1972, Plainview, N.Y.) to obtain strain AJ12739-ΔkefB. The strain AJ12739 has been deposited in the Russian National Collection of Industrial Microorganisms (VKPM) (Russia, 117545 Moscow, 1 Dorozhny proezd, 1) on Nov. 6, 2001 under accession number VKPM B-8197 and then converted to a deposit under the Budapest Treaty on Aug. 23, 2002.

Both *E. coli* strains, AJ12739-ΔkefB and AJ12739, can be cultivated at 37° C. for 18 hours in a nutrient broth, and 0.3 ml of the obtained cultures can each be inoculated into 3 ml of a fermentation medium in a 20×200-mm test tube and cultivated at 37° C. for 48 hours with shaking on a rotary shaker. After cultivation, the amount of phenylalanine which accumulates in the medium can be determined by TLC. The 10×15-cm TLC plates coated with 0.11-mm layers of Sorbfil silica gel containing no fluorescent indicator (Stock Company Sorbpolymer, Krasnodar, Russia) can be used. The Sorbfil plates can be developed with a mobile phase consisting of propan-2-ol:ethylacetate:25% aqueous ammonia:water=40:40:7:16 (v/v). A solution of ninhydrin (2%) in acetone can be used as a visualizing reagent.

The composition of the fermentation medium (g/l) is as follows:

| | |
|---|---|
| Glucose | 40.0 |
| $(NH_4)_2SO_4$ | 16.0 |
| $K_2HPO_4$ | 0.1 |
| $MgSO_4 \cdot 7H_2O$ | 1.0 |
| $FeSO_4 \cdot 7H_2O$ | 0.01 |
| $MnSO_4 \cdot 5H_2O$ | 0.01 |
| Thiamine HCl | 0.0002 |
| Yeast extract | 2.0 |
| Tyrosine | 0.125 |
| $CaCO_3$ | 20.0 |

Glucose and magnesium sulfate are sterilized separately. $CaCO_3$ is dry-heat sterilized at 180° for 2 hours. The pH is adjusted to 7.0.

Example 9

Production of L-Tryptophan by *E. coli* SV164 (pGH5)-ΔkefB

To test the effect of inactivation of the kefB gene on L-tryptophan production, DNA fragments from the chromosome of the above-described *E. coli* strain MG1655 ΔkefB::cat can be transferred to the tryptophan-producing *E. coli* strain SV164 (pGH5) by P1 transduction (Miller, J. H. Experiments in Molecular Genetics, Cold Spring Harbor Lab. Press, 1972, Plainview, N.Y.) to obtain the strain SV164(pGH5)-ΔkefB. The strain SV164 has the trpE allele encoding anthranilate synthase free from feedback inhibition by tryptophan. The plasmid pGH5 harbors a mutant serA gene encoding phosphoglycerate dehydrogenase free from feedback inhibition by serine. The strain SV164 (pGH5) is described in detail in U.S. Pat. No. 6,180,373.

Both *E. coli* strains, SV164(pGH5)-ΔkefB and SV164 (pGH5), can be cultivated with shaking at 37° C. for 18 hours in 3 ml of nutrient broth supplemented with tetracycline (20 mg/l, marker of pGH5 plasmid). The obtained cultures (0.3 ml each) can each be inoculated into 3 ml of a fermentation medium containing tetracycline (20 mg/l) in 20×200-mm test tubes, and cultivated at 37° C. for 48 hours with a rotary shaker at 250 rpm. After cultivation, the amount of tryptophan which accumulates in the medium can be determined by TLC as described in Example 8. The fermentation medium components are listed in Table 3, and are sterilized in separate groups (A, B, C, D, E, F, and H), as shown, to avoid adverse interactions during sterilization.

TABLE 3

| Groups | Component | Final concentration, g/l |
|---|---|---|
| A | $KH_2PO_4$ | 1.5 |
| | NaCl | 0.5 |
| | $(NH_4)_2SO_4$ | 1.5 |
| | L-Methionine | 0.05 |
| | L-Phenylalanine | 0.1 |
| | L-Tyrosine | 0.1 |
| | Mameno (total N) | 0.07 |
| B | Glucose | 40.0 |
| | $MgSO_4 \cdot 7H_2O$ | 0.3 |
| C | $CaCl_2$ | 0.011 |
| D | $FeSO_4 \cdot 7H_2O$ | 0.075 |
| | Sodium citrate | 1.0 |
| E | $Na_2MoO_4 \cdot 2H_2O$ | 0.00015 |
| | $H_3BO_3$ | 0.0025 |
| | $CoCl_2 \cdot 6H_2O$ | 0.00007 |
| | $CuSO_4 \cdot 5H_2O$ | 0.00025 |
| | $MnCl_2 4H_2O$ | 0.0016 |
| | $ZnSO_4 \cdot 7 H_2O$ | 0.0003 |
| F | Thiamine HCl | 0.005 |
| G | $CaCO_3$ | 30.0 |
| H | Pyridoxine | 0.03 |

Group A has pH 7.1 adjusted by $NH_4OH$. Each of groups A, B, C, D, E, F and H is sterilized separately, chilled, and mixed together, and then $CaCO_3$ sterilized by dry heat is added to the complete fermentation medium.

Example 10

Production of L-Proline by *E. coli* 702ilvA-ΔkefB

To test the effect of inactivation of the kefB gene on L-proline production, DNA fragments from the chromosome of the above-described *E. coli* strain MG1655 ΔkefB::cat can be transferred to the proline-producing *E. coli* strain 702ilvA by P1 transduction (Miller, J. H. Experiments in Molecular Genetics, Cold Spring Harbor Lab. Press, 1972, Plainview, N.Y.) to obtain strain 702ilvA-ΔkefB. The strain 702ilvA has been deposited in the Russian National Collection of Industrial Microorganisms (VKPM) (Russia, 117545 Moscow, 1 Dorozhny proezd, 1) on Jul. 18, 2000 under accession number VKPM B-8012 and then converted to a deposit under the Budapest Treaty on May 18, 2001.

Both E. coli strains, 702ilvA and 702ilvA-ΔkefB, can be grown for 18-24 hours at 37° C. on L-agar plates. Then, these strains can be cultivated under the same conditions as in Example 7.

Example 11

Production of L-Arginine by E. coli Strain 382-ΔkefB

To test the effect of inactivation of the kefB gene on L-arginine production, DNA fragments from the chromosome of the above-described E. coli strain MG1655 ΔkefB::cat were transferred to the arginine-producing E. coli strain 382 by P1 transduction (Miller, J. H. Experiments in Molecular Genetics, Cold Spring Harbor Lab. Press, 1972, Plainview, N.Y.) to obtain strain 382-ΔkefB. The strain 382 has been deposited in the Russian National Collection of Industrial Microorganisms (VKPM) (Russia, 117545 Moscow, 1 Dorozhny proezd, 1) on Apr. 10, 2000 under accession number VKPM B-7926 and then converted to a deposit under the Budapest Treaty on May 18, 2001.

Both E. coli strains, 382-ΔkefB and 382, were cultivated with shaking at 37° C. for 18 hours in 3 ml of nutrient broth. The obtained cultures (0.3 ml each) were each inoculated into 3 ml of a fermentation medium in 20×200-mm test tubes and cultivated at 32° C. for 72 hours on a rotary shaker.

After the cultivation, the amount of L-arginine which accumulates in the medium was determined by paper chromatography using the following mobile phase: butanol:acetic acid:water=4:1:1 (v/v). A solution of ninhydrin (2%) in acetone was used as a visualizing reagent. A spot containing L-arginine was cut out, L-arginine was eluted with 0.5% water solution of $CdCl_2$, and the amount of L-arginine was estimated spectrophotometrically at 540 nm. The results of ten independent test-tube fermentations are shown in Table 4.

The composition of the fermentation medium (g/l) was as follows:

| | |
|---|---|
| Glucose | 48.0 |
| $(NH4)_2SO_4$ | 35.0 |
| $KH_2PO_4$ | 2.0 |
| $MgSO_4·7H_2O$ | 1.0 |
| Thiamine HCl | 0.0002 |
| Yeast extract | 1.0 |
| L-isoleucine | 0.1 |
| $CaCO_3$ | 5.0 |

Glucose and magnesium sulfate are sterilized separately. $CaCO_3$ is dry-heat sterilized at 180° C. for 2 hours. The pH is adjusted to 7.0.

TABLE 4

| Strain | $OD_{540}$ | Amount of L-arginine, g/l |
|---|---|---|
| 382 | 11.4 ± 3.8 | 11.1 ± 0.4 |
| 382-ΔkefB | 12.6 ± 1.7 | 11.8 ± 0.6 |

As follows from Table 4, 382-ΔkefB produced a higher amount of L-arginine, as compared with 382.

While the invention has been described in detail with reference to preferred embodiments thereof, it will be apparent to one skilled in the art that various changes can be made, and equivalents employed, without departing from the scope of the invention. All the cited references herein are incorporated as a part of this application by reference.

INDUSTRIAL APPLICABILITY

According to the present invention, production of L-amino acid of a bacterium of the Enterobacteriaceae family can be enhanced.

The invention claimed is:

1. A method for producing an L-amino acid comprising:
cultivating an L-amino acid producing bacterium of *Escherichia coli* or *Pantoea ananatis* in a medium, and collecting said L-amino acid from the medium,
wherein said bacterium has been modified to attenuate expression of the kefB gene on the chromosome of said bacterium by a method selected from the group consisting of
A) deleting a part of said gene,
B) shifting the reading frame of said gene,
C) introducing missense/nonsense mutation(s) into said gene,
D) modifying a region controlling expression of said gene, and
E) combinations thereof,
wherein, prior to being modified, the kefB gene encodes a protein having potassium efflux activity.

2. The method according to claim 1, wherein said L-amino acid is selected from the group consisting of an aromatic L-amino acid and a non-aromatic L-amino acid.

3. The method according to claim 2, wherein said aromatic L-amino acid is selected from the group consisting of L-phenylalanine, L-tyrosine, and L-tryptophan.

4. The method according to claim 2, wherein said non-aromatic L-amino acid is selected from the group consisting of L-threonine, L-lysine, L-cysteine, L-methionine, L-leucine, L-isoleucine, L-valine, L-histidine, glycine, L-serine, L-alanine, L-asparagine, L-aspartic acid, L-glutamine, L-glutamic acid, L-proline, and L-arginine.

5. The method according to claim 1, wherein expression of the kefB gene is attenuated by inactivation of the kefB gene in said bacterium.

6. The method according to claim 1, wherein said kefB gene encodes a protein having a homology of not less than 95% to the entire amino acid sequence of SEQ ID NO: 2.

* * * * *